United States Patent [19]

Hurion et al.

[11] Patent Number: 4,732,758
[45] Date of Patent: Mar. 22, 1988

[54] PREPARATION WITH COLLAGENOLYTIC ACTIVITY HAVING HIGH ACTIVITY AND PHARMACEUTICAL COMPOSITIONS CONTAINING IT

[75] Inventors: Nicole Hurion, Paris; Borivog Keil, Gif/S/Yvette, both of France

[73] Assignee: Institut Pasteur, Paris, France

[21] Appl. No.: 647,674

[22] Filed: Sep. 5, 1984

[30] Foreign Application Priority Data

Jan. 5, 1983 [FR] France .................. 83 00114
Jan. 5, 1983 [FR] France .................. 83 00112

[51] Int. Cl.$^4$ .................. A61K 37/62; A61K 7/28
[52] U.S. Cl. .................. 424/94.2; 424/50
[58] Field of Search .................. 424/94, 50, 94.2

[56] References Cited

U.S. PATENT DOCUMENTS

| 3,003,917 | 10/1961 | Beiler et al. | 424/94.2 |
|---|---|---|---|
| 3,296,094 | 1/1967 | Cayle | 426/63 |
| 3,677,900 | 7/1972 | Merkel | 424/94 |
| 4,200,626 | 4/1980 | Okuda et al. | 424/49 |
| 4,329,430 | 5/1982 | Klein et al. | 424/94.2 |
| 4,524,065 | 6/1985 | Pinnell | 424/94.2 |
| 4,543,329 | 9/1985 | Daum et al. | 435/172.3 |

FOREIGN PATENT DOCUMENTS

| 0005132 | 7/1967 | France | 424/94.2 |
|---|---|---|---|
| 1,579,878 | 8/1969 | France | 424/94.2 |
| 802069 | 9/1958 | United Kingdom . | |

OTHER PUBLICATIONS

Keil et al., "Specificity of Collagenase from *Achromobacter Iophagus*", FEBS Letters, vol. 56, No. 2, Aug. 1975.
Microbiology Abstracts, vol. 11, No. 3, (1976-3), "Specificity of Collagenase from Acromobacter Iophagus", 11B2273, B. Keil et al.
Microbiology Abstracts, vol. 11, No. 3, (1976-3), "Purification, Stability and Inhibition of the Collagenase from Achromobacter Iophagus", 11B2274, A. Lecroisey et al.

Primary Examiner—Delbert R. Phillips
Assistant Examiner—Nathan M. Nutter
Attorney, Agent, or Firm—Burns, Doane, Swecker & Mathis

[57] ABSTRACT

The invention relates to a pharmaceutical composition containing in association with a pharmaceutical vehicle a collagenase of high specific activity and capable of being inhibited at least partly by myosine. It is useful for the treatment of pathologies manifested by an uncontrolled alteration of the collagen-rich structures in man or animal.

17 Claims, 2 Drawing Figures

PREPARATION WITH COLLAGENOLYTIC ACTIVITY HAVING HIGH ACTIVITY AND PHARMACEUTICAL COMPOSITIONS CONTAINING IT

This application is a continuation of International Application No. PCT/FR84/00004 filed Jan. 5, 1984, now abandoned.

The invention relates to a preparation with collagenolytic activity, more particularly to pharmaceutical compositions containing this preparation, in association with a pharmaceutical vehicle, particularly for use in the treatment of pathologies manifested by an uncontrolled alteration in the structures rich in collagen, in man or animal.

Several types of micro-organisms producing collagenolytic enzyme or "collagenase" have already been described in the literature. It is however often difficult to control the active constituent contents of these preparations. These preparations can besides not be free of a certain number of toxic constituents, for example neurotoxins, which render them unsuited for use in compositions intended to be pharmaceutical.

It is an object of the invention to provide a pharmaceutical composition permitting selective enzymatic activity with respect to pathogenic collagenic structures when applied to lesions manifested by uncontrolled alteration of collagen. It is also an object to produce compositions in which the relative proportions of the principal constituents of the collagenolytic preparation are equilibrated in predetermined proportions as a function of the quality of the desired therapeutic results.

The pharmaceutical composition according to the invention comprises an effective dose of a collagenase of high specific activity recognising specifically an X-glycyl-L-prolyl peptide sequence, in which X is a natural amino acid residue linked to the N-terminal end of the glycyl residue. The peptide sequence is cut specifically by the collagenase at the X-glycyl linkage. Moreover, the collagenase is inhibited at least partly by myosin.

A preferred collagenase for use in the pharmaceutical composition according to the invention can be obtained from cultures of *Vibrio alginolyticus chemovar iophagus*, of which the principal taxonomic characteristics will be recalled below, or from any micro-organisms derived from the latter or capable like the latter of producing such a collagenase. More generally still, collagenases which can be employed in the pharmaceutical composition according to the invention are those which are capable of reacting with selective antibodies prepared against the collagenase called "Achromobacter collagenase" listed under the number EC. 3.4.24.8 in "Enzyme Nomenclature Edition IUPAC-IUB (1978). This collagenase is obtained from the strain of *Vibrio alginolyticus chemovar iophagus* which has been deposited in the National Collection of Micro-organism Cultures of the PASTEUR INSTITUTE (C.N.C.M.) under number I-029.

This collagenase is distinguished from other known collagenases by its high specific activity. The latter can reach 2 units microkatal/mg (μkat/mg) of protein. It has been described, for example, in the article entitled "Subunit structure of Achromobacter Collagenase", of V. KEIL-DLOUHA and B. KEIL, which appeared in Biochim. Biophys. Acta 522, 218–228 (1978).

Reference can also be made, as regards the chemical characterization of this enzyme as well as of the producing micro-organism, to the articles entitled "Chemical characterization and study of the autodigestion of pure collagenase from *Achromobacter iophagus*" of Vera KEIL-DLOUHA, which appeared in Biochimica et Biophysica Acta, 429 (1976) 239–251, and "Some newly characterized collagenases from procaryotes and lower eucaryotes" of Borivoj KEIL, which appeared in Molecular & Cellular Biochemistry, Jan. 26, 1979, volume 23, nr. 2.

Figure 1:
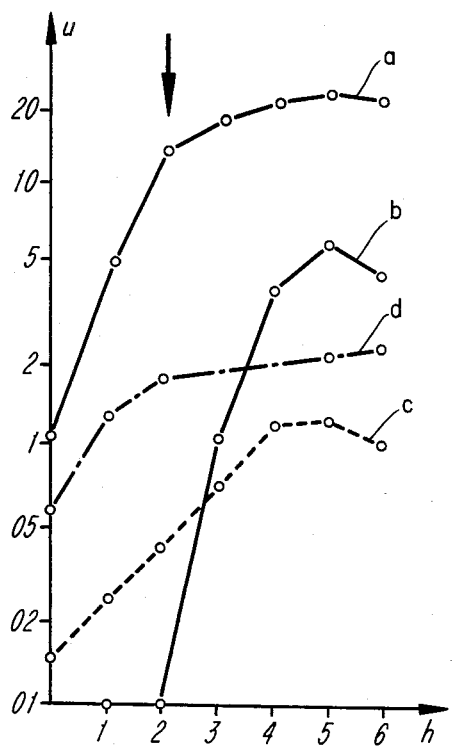
FIG. 1 is a graph depicting as a function of time (a) cellular growth, (b) collagenase activity (c) caseinolytic, and proteinase activity and (d) nuclease activity.

The invention relates more particularly to pharmaceutical compositions containing doses expressed by activity of the collagenase, related to the total weight of the composition, at least equal:

- to 0.05 μkat/g of the pharmaceutical composition for emulsions, pomades, powders or any compositions not truly liquid, in the sense usually given to this expression, and
- to 0.05 μkat/ml of the pharmaceutical composition for solutions formulated for topical use.

Preferred pomades according to the invention contain particularly from 0.1 to 2, preferably from 0.5 to 1 μkat of collagenase per gram of pomade.

Preferred solutions for topical applications according to the invention contain from 0.1 to 2, preferably 0.5 to 1 μkat of collagenase per ml of solution.

Advantageous compositions according to the invention contain in addition, on the one hand, neutral proteases and, on the other hand, endonucleases.

Preferably, the proportions of proteases and endonucleases with respect to 0.350 μkat of collagenase do not exceed 200 caseinolytic units for proteases and 500 nucleasic units for endonucleases.

Suitable compositions for application of the invention contain the three types of constituents, preferably in the relative proportions corresponding:

- to at least 0.350 μkat of collagenase,
- to 20 to 200 caseinolytic units as regards their content of neutral proteases and
- 30 to 500 nucleasic units, as regards the endonucleases.

In still more preferred compositions, the relative proportions with respect to one another of the above constituents correspond respectively to activities:

- of at least 0.350 μkat as regards collagenase,
- of 20 to 50 caseinolytic units as regards the neutral proteases and
- 30 to 60 nucleasic units, as regards endonucleases.

The use of the compositions according to the invention in the treatment of lesions of the above indicated type (for example burns, ulcers, eschars, hard eschars or white eschars based on collagen, cheloids, such as those produced after surgical operations) has been found to be particularly beneficial.

In its therapeutic action, the composition according to the invention preferentially decomposes the collagen of the conjunctive tissue. It does not attack the muscular mass, in particular the myofibrils of the muscles, its collagenolytic component being inhibited by the myosin of the muscle. The composition according to the invention will sometimes, below, be called "Achromase" particularly when it contains proteases and endonucleases, especially in the above-indicated proportions, in addition to the collagenase.

The action of Achromase is characterized by the production, from macromolecular substrates of the necrosis, of fragments which have chemotactic action on the blood elements. It is by this chemotactic action that in particular the macrophages and the leucocytes are accumulated at the periphery of the zone of action of Achromase. This accumulation of the elements of the blood is favorable to the process of tissue regeneration (for example, in ulcers, in tissues damaged by burns).

Another characteristic of the action of Achromase with respect to tissues altered to a necrotic character is that it stops at the level of the living tissue. The action of the Achromase stops after having decomposed the dead tissue at the limit of the living tissue. It does not cause, by the action of its proteolytic components, lesions of the living tissue. These effects are produced particularly due to the inhibition systems which exist in the living tissue, particularly to the three systems involving:

(1) collagenase—inhibitors of a polypeptidic nature present in the undamaged tissue,
(2) the myosin present in the muscular tissue, and
(3) nonspecific inhibitors of collagenase proteases, in particular of $\alpha_2$-macroglobulin, present in the blood stream.

It is in this respect important to stress that to be effective the pharmaceutical compositions must have a high collagenolytic activity, having particularly the orders of magnitudes which have been indicated above. It has in fact been established that, contrary to what could have been feared, the selectivity of action of the collagenolytic preparation of the invention with respect to only necrosed tissues or, more generally, any unhealthy tissue, was not affected even at high doses of collagenase. In fact the natural barriers that healthy tissue offers against the action of collagenase or regulators of the activity of the latter that the natural barriers contain, were found to be fully effective against what could a priori be considered as an "overdose" of the enzyme.

The neutral proteases, which form the second active constituent of Achromase, complete the action of the collagenase by degrading still further the fragments of the initial collagenolytic molecular substrate. When the preparation employed in the pharmaceutical composition according to the invention originates from *Vibrio alginolyticus chemovar iophagus*, said proteases are devoid of undesirable constituents.

Finally, the third constituent of Achromase, essentially formed of endonucleases, contributes to the destruction of the DNA releasable by the cells on the occasion of an infectious process, e.g., the pus of which the DNA released forms a larger part.

Preferably, the proteases and the endonucleases associated with the collagenase come from the same micro-organisms, and are obtained simultaneously with the collagenase in the culture media of the micro-organism.

The conditions under which the mutual proportions of these constituents can be adjusted are described below.

The invention relates also to preferred collagenolytic compositions in which the above-said collagenase is associated with effective preparations of hydrolysate of collagen, particularly enzymatic hydrolysate of collagen.

Essentially these hydrolysates are composed from collagen fragments, for example from calf skins composed of peptide molecules of which the average molecular weights are less than 10,000 daltons and particularly between 6,000 and 8,000 daltons. These hydrolysates can also be characterized by certain of their constituent amino acids and more particularly by the presence of hydroxy-proline. For example, a characteristic collagen hydrolysate comprises the following amino acids (originating from collagen) in the following proportions:

glycine: 33%
proline: 8.4%
hydroxyproline: 11.4%

These collagen hydrolysates can be obtained by any suitable fragmentation process of the denatured or undenatured collagenase. The term "hydrolysate" is not limited to products obtained by chemical or enzymatic hydrolysis of denatured or undenatured collagen. The hydrolysates of the type concerned are for example obtained by atomising gelatin.

It is to be noted that these collagen hydrolysates are of the same nature as the products resulting from the degradation of fibrous or necrotic collagen contained in wounds that the collagenolytic compositions according to the invention seek to hydrolyse.

It has been observed that the addition to the collagenase of the invention of substantial proportions of collagen hydrolysate such as mentioned above is manifested by an increase in the curative activity of the compositions according to the invention.

Another very important advantage of the addition of these collagen hydrolysates to the collagenase compositions according to the invention resides in the considerable increase in the stability on storage of the collagenolytic compositions according to the invention. This increase in stability is manifested particularly fully on the occasion of the lyophilisation of collagenase preparations according to the invention. It will hence be particularly interesting to associate these collagen hydrolysates, very soluble in the cold, with collagenase preparations in the terminal phase of the preparation of the latter. In particular these collagen hydrolysates can be added directly to collagenase solutions obtained from culture media of the producing micro-organism. It is particularly desirable to add the collagen hydrolysates to the collagenase solutions after carrying out additional ultra-filtration and purification operations of the solutions obtained, which are required to remove undesirable insoluble and soluble constituents contained in the culture media removed, but before the final freeze drying of the collagen preparations obtained.

Preferred pharmaceutical compositions of the invention contain collagen hydrolysates and collagenase in the proportion of 1 to 25 mg, preferably 2 to 10 mg of collagen hydrolysate per 1 mg of collagenase. It is also possible to express preferred ratios in the following manner. The preferred compositions contain from 1 to 25, particularly from 2 to 10, for example 5 mg of collagen hydrolysate per microtal of collagen.

It goes without saying that these ranges of proportions apply without distinction to the case where the collagen is associated or to the case where it is not associated with the above-indicated proteases and endonucleases.

The pharmaceutical composition according to the invention hence plays an essential role where tissue wastes which tend to accumulate in the region of lesions of the type concerned are destroyed, this destruction (detersion) necessarily preceding the start of the natural or induced cicatrisation, for example by graft.

The invention relates also to a process for the production of an active preparation according to the invention, containing more particularly three types of constituents which have been envisaged above. This process employs more particularly the aerobic bacteria *Vibrio alginolyticus chemovar iophagus*. This process consists of cultivating this micro-organism under conditions known in themselves and inducing also in a manner known in itself the production of collagenase by the addition to the culture medium of a suitable inductor, more particularly collagen or collagen fragments having a molecular weight still sufficient to form a secondary structure characteristic of the helicoidal collagen chains. This culture is continued until after induction in the culture medium of production of said neutral proteases, the culture being interruptable when the relative proportions of collagenase and proteinase have reached desired values comprised within the above-indicated respective intervals, the active preparation then being recoverable by techniques known in themselves from the culture medium. In particular, it is possible, after removal of the cells, to precipitate proteins from the supernatant liquor with a sufficient concentration of ammonium sulfate which can, for example, reach 60% of the saturation level of this salt in solution. The precipitate replaced in suspension can be dialysed against distilled water to remove the ions extracted in the course of the precipitation, before being finally freeze dried. As a modification, the active principle can be purified by ultrafiltration.

In the foregoing, it is by modifying the duration of the culture that it has been proposed to adjust the relative proportions of collagenase or of protease (or proteinase). It can also be envisaged to supplement the collagenase with proteinases and endonucleases of external origin, or on the contrary of withdrawing the excess of proteinase and endonuclease for the case where this solution could be purified, having regard to the increased yield of collagenase that could be expected from a prolongation of the time of culture.

This latter operation can be carried out by taking advantage of the very different molecular weights of the collagenase and the proteinases: In particular, these molecular weights are higher than 30,000 for collagenase and less than 30,000 for proteases, so that their separation is easy, for example on suitable ultrafiltration membranes. In particular, the culture medium obtained after interruption of the culture and separation of the bacteria, can be the subject of three successive ultrafiltrations, the first being in order to remove the residual bacteria and obtain a clear liquid containing collagenase and proteases, the second being on an ultrafiltration membrane separating the proteins from the higher molecular weights, at 30,000, particularly the collagenases and the third being on a filtration membrane enabling the separation of molecular weights higher than 10,000, which enables the proteases to be recovered. The collagenase and the proteases can then be remixed in the desired proportions.

In accordance with the additional feature already mentioned above of the invention it is advantageous prior to recovery of collagenases which are further purified by freeze drying to add collagen hydrolysates prior to the freeze-drying, preferably in the proportions which have been indicated. In other words it is those solutions supplemented with collagen hydrolysates, which are then subjected to freeze drying.

The addition of these collagen hydrolysates to a collagenase in solution before its recovery from this solution, can be analyzed as representing an essential step of a process seeking to stabilize said collagenase. This stabilization process is hence characterized by the step which constitutes the lyophilisation of the solution containing the collagenase, in the presence of the abovesaid collagen hydrolysates, taken preferably in the relative proportions which have been indicated above with respect to collagenase.

To assay the various constituents of the composition, recourse may be had to the techniques described below which employ the substrates, the reagents and the methods of calculation also mentioned below.

ASSAY OF THE COLLAGENASE (Wunsch E. and Heidrich H. G. (1963) Z. fur Physiol. Chem. 333, 149–151)

SUBSTRATE

The substrate used was 4-phenylazo-benzyloxycarbonyl-L-Pro-Leu-Gly-L-Pro-D-Arg. HCl (PZ-PLGPR), marketed by the Fluka Company.

REAGENTS

The reagents employed where the following:
A. Buffer:
  the buffer was formulated from the following three solutions:
    solution A1: prepared from 160 mM of veronal (sodium salt of 5.5-diethylbarbituric acid) and 143 mM of sodium acetate, $3H_2O$;
    solution A2: 1N HCl;
    solution A3: 8.5% NaCl;
  the buffer was obtained by mixing 200 ml of solution A1 with 80 ml solution A3, and by adjusting the pH to 8.5 with the solution A2. It was up to one liter by adding water and $CaCl_2$, $2H_2O$ was added to obtain a final concentration of 4 mM.
B. Substrate solution:
  It was obtained by dissolving 10 mg of PZ-PLGPR in 100 μl of methanol. Buffer was added to bring it to 10 ml and the substrate solution so obtained remained stable for one week.
C. Collagenase sample:
  The collagenase sample was obtained by preserving 1 mg of solution in 1 ml of buffer; by means of samples of unknown specific activity. It was diluted according to the preliminary readings. The optimal dilutions must give colorimetric values of the optical density at 320 nm (see below) within the range of 0.1 to 1.0.
D. Citric acid:
  It was formed of a 0.5% solution in water.
E. Ethyl acetate.

ASSAY TECHNIQUE

It proceeded as follows:
1. the solution B was preheated to 37° C.;
2. 0.1 ml of the collagenase solution (correctly diluted) was mixed with 0.4 ml of preheated solution B and the solution was incubated for 15 min. at 37° C.
3. 1 ml of solution D was added and 4. 5 ml of ethyl acetate were added and vigorous mixing was carried out.
5. The upper organic layer was then removed and it was dried by adding anhydrous $Na_2SO_4$;
6. The optical density at 320 nm was measured with respect to that of a control obtained under the same conditions as the sample studied, by the procedure indicated under points 1 through 5, except that buffer was used in place of the substrate (solution B).

METHOD OF CALCULATION

1 Wunsch-Heidrich unit =

$$\frac{\text{optical density at 320 nm (relating to 0.1 ml of sample)}}{0.044}$$

Specific activity of the sample expressed in katals $= \frac{0.2525 \times \text{optical density at 320 nm}}{mg}$ in $nkat$/mg 1.0 μkat = 90,000 WH units The coefficient was deduced from a calibration curve obtained with the product which cuts up the peptide (PZ-Pro-Leu) (compound B marketed by Fluka).

II DETERMINATION OF THE PROTEASES (Laskowski M. (1955) Methods in enzymology II, 32; Kunitz M. (1947) J. Gen. Physiol. 30, 291)

SUBSTRATE

The substrate used was casein for biochemical use (marketed by Merck, under number 2 244).

REAGENTS

The reagents used were as follows:
solution A:
it was composed of:
  Aa: boric acid 0.2M (12.4 g/1,000 ml);
  Ab: 0.05 borax (19.05 g/1,000 ml); To obtain solution A, 100 ml of solution Aa were adjusted to pH 7.6 by means of solution Ab (about 4 ml);
solution B:
  1 g of casein was suspended in 100 ml of solution A. It was heated in a water bath to 100° C. until completely dissolved (about 15 min). The opalescent solution so obtained can be stored for a week at 4° C.;
solution C:
  5% trichloroacetic acid in water.

PROTEINASE SAMPLE

Dilution of samples containing proteinase must be adjusted according to the preliminary assay to an equivalent of 2–10 μg of trypsin/ml.

ASSAY TECHNIQUE

It proceeded as follows:
1. the tubes were prepared (Vidal plastic tubes 11×70), in number corresponding to twice the number of samples, in order that to each sample there may correspond its own control;
2. 0.5 ml of solution B were preincubated in each tube, for 5 min at 37° C.;
3. to each "sample" tube, were added 0.5 ml of sample. It was incubated for 20 min at 37° C. with stirring; 1.5 ml of solution C were added;
4. To each control tube were added 1.5 ml solution C. It was incubated 5 min at 37° C. and 5 ml of sample was added;
5. All the tubes were left at 4° C. throughout the night.
6. It was centrifuged for 10 min at 8,000 rpm at room temperature.
7. the optical density at 280 ($OD_{280}$) of the supernatant liquid of the sample with respect to the corresponding control was read.

CALCULATION

1. Calibration curve:
A stored solution of pure trypsin was diluted (0.1 mg/ml of HCl $10^{-3}$M) to obtain final concentrations of 1, 2, 4, 6, 8 μg of trypsin per ml. Then the steps 1 to 7 mentioned in the preceding paragraph were carried out.
2. One unit of activity corresponds to 1 μg of trypsin; one unit of specific activity corresponds to 1 μg of trypsin per mg of protein.

III DETERMINATION OF DEOXYRIBONUCLEASE (Kunitz M. (1950) J. Gen. Physiol. 33, 349–363)

REAGENTS

The reagents used were as follows:
deoxyribonuclease I (marketed by BOEHRINGER) of quality II (2,000 U/mg);
deoxyribonucleic acid (marketed by BOEHRINGER) at 3 ml/10 mg.

BUFFER

The buffer was formulated as follows: 100 mM of Tris. HCl; 4 mM of $MgSO_4$; $7H_2O$; 1.8 mM of $CaCl_2.2H_2O$ were adjusted to pH 7.5 with hydrochloric acid.

SOLUTIONS

Standard enzyme: 1 mg of deoxyribonuclease I was dissolved in 1 ml of buffer.
Substrate: 150 μl in 50 ml of buffer was diluted.

ASSAY TECHNIQUE

It proceeded as follows:
1. the absorbance at 260 nm of 3 ml of substrate solution was adjusted to 0.
2. 100 μl of standard enzyme were added and mixed;
3. the variation in absorbance over 10 min was recorded.
4. The ratio $\Delta A_{260}$ was determined (variation of absorbance at 260 nm)/min;
5. Steps 1 to 4 are repeated with fresh substrate solution and an unknown enzyme sample and the value of $\Delta A_{260}$/min was determined.

CALCULATION mg/ml = optical density at 280 nm ($OD_{280}$)×0.9

$$\text{Units per mg of protein} = \frac{\Delta A/\text{min} \times 1,000 \times 6}{\text{mg of enzyme used}}$$

IV DETERMINATION OF PROTEINS (Lowry H. O., Roseborough N. J. and Randall R. J. (1951), J. Biol. Chem. 193, 265)

REAGENTS

The reagents used were as follows:
solution A: 2% $Na_2CO$ in 0.1M NaOH;
solution B: 2% Na, potassium tartrate;

solution C: 1% CuSO$_4$;

solution D: 1 ml of solution B+1 ml of solution C, diluted to 100 ml with solution A;

solution D: foline reagent diluted to 1/1.

CALIBRATIONS CURVE

1. The reference protein solution was prepared from 1 mg of bovine albumin serum (BSA, marketed by Sigma) in 2 ml of water.

2. A series of reference solution dilutions were prepared from 10 to 80 μl to a final volume of 400 μl in water.

3. 2 ml of solution D were added. It was mixed and left for 10 min at the temperature of the laboratory;

4. 200 μl of solution E were added. It was left to incubate in darkness at 50° C. for 10 min;

5. The optical density at 750 nM was read with respect to the control (water instead of the assay solution used in step 2). In this way the calibration curve was constructed.

DETERMINATION

The unknown sample was treated at different dilutions (final volume 400 μl, step 2).

CALCULATIONS

The protein content of the unknown sample was expressed as equivalent in weight of reference bovine albumin serum (BSA).

Figure 2:
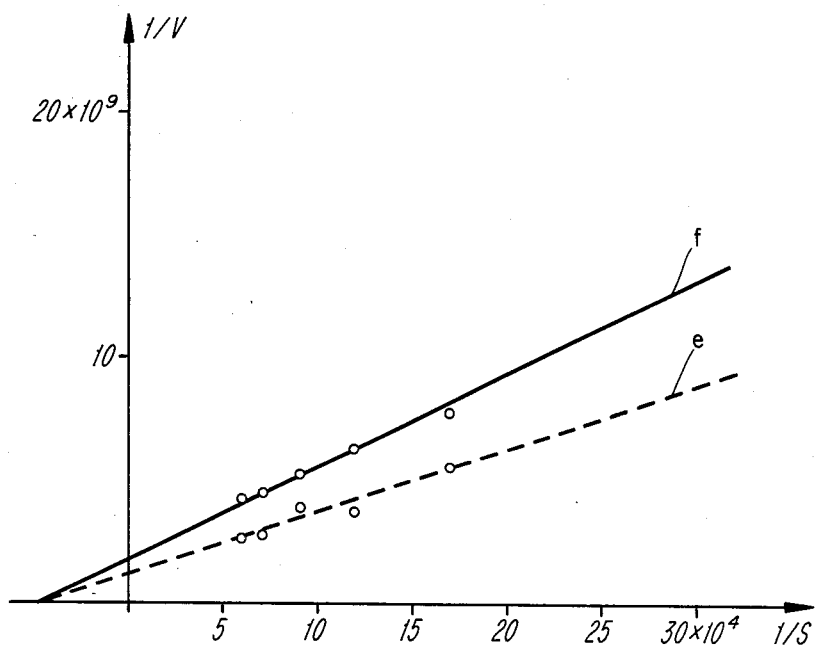
FIG. 2 is graph depicting (e) the inverse of the number of moles of collagen digested per hour at 37° C. in the absence of myosine and (f) in the presence of 5 mg. of myosine as a function of the inverse of the number of moles of collagen employed.

Other features of the invention will appear also in the course of the description which follows of the culture conditions of *Vibrio alginolyticus chemovar iophagus*. Reference will be made to the figures in which:

FIG. 1 depicts curves representing relative concentrations of different enzymes produced by culturing the abovesaid bacteria, as a function of time;

FIG. 2 depicts comparative curves aiming at establishing the inhibiting character of myosine with respect to collagenase.

The *Vibrio alginolyticus chemovar iophagus* strain is voluntary aerobic and appears in the form of gram negative rods 2-2.5 μm in length and 1-1.5 μm in width, motile by means of single polar flagellae. It forms round and yellow colonies 2-3 mm in diameter, after incubation at 30° C. for one night on a thiosulfate-citrate-bile-sucrose medium (TCBS).

It has a positive response in the following tests: cytochrome oxydase, Voges-Proskauer reaction, indole production, lysine decarboxylase, gelatinase (skin test), esterase of the wetting agent marketed under the name TWEEN 80, tetrathionate reductase, nitrate reduction, production of acid from glucose, maltose, mannitol, sucrose, trehalose, mannose and glycerol, citrate utilization (Simmons). It is sensitive to the action of aminoglycosidic antibiotics, to chloramphenicol, tetracyclines, colistine, rifampicine, to sulfonamides, to nalixide acid, to nitrofurantoin and to the vibriostatic agent 0/129 in the disk test, but it resists trimethoprime.

It gives a negative response in the following tests: reaction to methyl red, arginine dihydrolase, urease, phenylalanine deaminase, ONPG test, production of H$_2$S (Kligler iron agar), production of gas from glucose, production of acid from xylose, arabinose, adonital, rhamnose, sorbose, sorbitol, dulcitol, lactose, inositol, salicine, raffinose, mellibiose, α-methylglucoside, mucate. It does not use malonate.

The strain I-029 is very halophilic with an optimum growth which occurs in 13% sodium chloride and an apparent tolerance to 15% sodium chloride. It is also fully resistant to ampicilline, carbenicilline, in part to cephalotine. It shows positive reactions in tests with ornithine decarboxylase and in cellobiose fermentation tests.

CULTURE CONDITIONS

The cells were cultivated under stirring and forced aeration (1.4 atmospheres) at 30° C. in a medium containing 0.1M Tris. HCl, 0.4NaCl, 2 mM of CaCl, at pH 7, containing 2.5% casamino acids (Difco Labs., Detroit, Mich.). Two hours after the start of the culture, there was added to the medium the composition marketed under the name ASF (fragments of calf skin collagen peptide; average molecular weight 7000, ROUSSELOT S.A., France) to obtain a concentration of 1.5% by weight. For the controls of growth, the turbidity was measured by absorbance per cm at 600 nm in samples extracted at one hour intervals.

PRODUCTION OF COLLAGENASE, PROTEINASE AND NUCLEASE

The strain produced caseinolytic proteinase extra-cellular nuclease and, as soon as ASF has been added, collagenase. The activity level of the collagenase then rises to reach 60 nkat/ml.

The curves of FIG. 1 are representative as regards:

curve a, cellular growth, curve b, collagenase activity, curve c, the activity of the caseinolytic proteinase, and curve d, the activity of the nuclease, as a function of time.

The culture is preferably interrupted, when the activity of the collagenase passes through a maximum, particularly after five hours in the case shown. The collagenase was concentrated and recovered from this medium. It can be further purified as described in the book of KEIL-DLOUHA, V. 1976, "Chemical characterization and study of the autodigestion of pure collagenase from *Achromobacter iophagus*, Biochem. Biophys. Acta, 429, 239-305 and of LECROISEY A., V. KEIL-DLOUHA, D. R. WOODS, D. PERRIN and B. KEIL, 1975, "Purification, stability and inhibition of the collagenase from *Achromobacter iophagus*, FEBS Letters 59, 167-172.

A typical preparation of Achromase contains 0.312 mg of protein (dry weight) per mg of the total product. It is characterized by the following relative activities, per mg of dry weight of protein:

collagenase: 0.554 μkat proteases: 145 caseinolytic units endonucleases: 477 nucleasic units

STABILIZATION OF COLLAGENOLYTIC ACTIVITY

The introduction in a collagenase solution of collagen hydrolysate has the effect of stabilizing the collagenolytic activity when the preparation is freeze dried. The effects of this stabilization, expressed in percentages of preservation of enzymatic activity of a collagenase preparation, before and after freeze drying, have been evaluated in tests in which there were employed variable proportions of collagen hydrolysate with respect to a particular dose of collagenase. The collagen hydrolysate used was that marketed in France under the name ASF by Etablissement Rousselot S.A. It is an atomized gelatin soluble in the cold in water.

The results obtained are indicated in the table below for the relative proportions of Achromase and of ASF which result from the left hand column of the table.

| ENZYMATIC ACTIVITY IN % | | |
|---|---|---|
| Achromase:ASF | Before freeze-drying | After freeze-drying |
| 1:0 | 100 | 50 |
| 1:1 | 100 | 63 |
| 1:5 | 100 | 96.6 |
| 1:10 | 100 | 94 |
| 1:25 | 100 | 78 |

It follows from examination of this table that:
the freeze-drying of an Achromase solution, in the absence of ASF, resulted in a 50% loss of collagenolytic activity and
the addition of ASF substantially reduced the losses of activity.

Particularly favorable results were observed for proportions of 2 to 10 parts by weight of ASF with respect to 1 part by weight of Achromase. For the proportion of 5 parts of ASF to one part of Achromase there was observed an almost complete preservation of the enzymatic activity of the initial solution.

To preserve the enzymatic activity in the course of freeze drying and to confer remarkable added stability there is also added to the preparations of freeze dried collagenase the hydrolysates of collagen, when the freeze dried collagenase is stored. It has thus been observed that the loss of collagenolytic activity, in percent, at the temperature of 4° C., was of 25% for a collagenase free from collagen hydrolysate after seven months. After the same period and at the same temperature the collagenolytic activity of collagenase preparations containing from 1 to 10 parts by weight of collagen hydrolysate for one part by weight of collagenase was preserved to 100%.

The same effects of collagenolytic hydrolysates on stability were observed at the temperature of 20° C. instead of 4° C. Thus, after seven months there was a loss of activity of 30% for the collagenase preparation free from collagenolytic hydrolysates and 5% only for preparations containing the same proportions of collagenolytic hydrolysate as above.

Similar stabilizations have been observed in other types of preparations based on collagenase (or Achromase), particularly when the latter are in ready-for-use form, such as those which will be considered below.

BIOLOGICAL PROPERTIES

The collagenase preparations obtained show, besides their above-indicated collagenolytic activity, the characteristic of being inhibited by myosine, which plays the role of non-competitive inhibitor for the collagenase. This property can be exploited by techniques employing the kinetic study of the effect of myosin on the activity of collagenase with respect to collagen.

The degradation of the collagen by the collagenase is followed by the determination of the hydroxyproline released after hydrolysis of the collagenase fragments solubilized by digestion.

Hydroxyproline being a specific amino acid of collagen, the other proteins contained in the reaction mixture do not interfere during the assay.

The mixture below was incubated in a 0.02M Tris. HCl, 0.23M NaCl, $5\times10^{-3}$M CaCl$_2$ buffer, pH 7.4 for one hour at 37° C.:

muscular collagen fiber 5 to 30 mg,
collagenase at 0.1 mg/ml in CaCl $10^{-4}$: 1 ml
incubation buffer or
myosine suspension at 5 mg/ml in this same buffer: 5 ml.

After incubation, the reaction mixture was centrifuged 5 minutes at 12,000 g, 0.5 ml of the supernatant liquor was hydrolysed overnight at 110° C. with 0.5 ml of 12N HCl. The samples were then evaporated under vacuum and taken up again with one volume of water so that the determination of the hydroxyproline was made possible.

The result of such a test with collagenase of titer 0.098 μkat/ml is illustrated by the curves of FIG. 2, in which the curve e is representative of the variations of the ratio 1/v (v representing the number of moles of collagen digested per hour at 37° C.) as a function of the ratio 1/s (s representing the number of moles of collagen employed), placed in the presence of collagenase, in the absence of myosine (interpretation according to LINWEAVER BURK).

The curve f is representative of the development of the digestion of the same preparations respectively in the presence of 5 mg of myosine.

Examination of these curves shows the very significant effects of the inhibition of the activity of the collagenase preparations concerned with respect to the collagen.

The collagenase employed according to the invention is devoid of any toxicity. This can be demonstrated by study of the lethal doses carried out in a mouse according to the method of J. T. LICHTFIELD and F. W. WILCOXON.

The LD-50s measured with a preparation injected intravenously with collagenolytic activity according to the invention, titrating 0.17 μkat/mg of protein, were the following:
8.58 mg/kg of mouse, which corresponds to
1.46 μkat per kg of mouse, when this lethal dose is related to the collagenolytic activity units of the preparation.

The remarkable collagenolytic activity of the preparations according to the invention has been demonstrated in pharmacological in vivo tests indicated below.

These tests consisted of the treatment, with a preparation containing the collagenase according to the invention, of burns previously formed on the skin of pigs, by the application of water at the temperature of 80° C., at several points on the back of these animals for 15 seconds (6 lesions on the right side and 6 lesions on the left side of the pigs). The dead epidermis was then removed from the scalded surfaces and the lesions were exposed to air for 48 hours. Each lesion had a diameter of the order of 3.8 cm. Tests carried out with the pomade containing collagenase were duplicated by tests carried out with a similar pomade, but which was devoid of collagenase, this pomade having been used as a control.

The compositions of these pomades were the following:
For the control pomade:

| polyoxyethylenic alcohol | 13 g |
|---|---|
| vaseline oil | 20 g |
| water | 100 g |
| sodium hydroxyde to adjust the pH to 7. | |

The pomade containing the collagenase contained the same excipients, and 0.25 μkat of collagenase per g of pomade.

The pomade containing the collagenase was applied to the lesions on the right side of the pigs, the control pomade on those of the left side.

The pomade applications were repeated respectively 3 days, 4 days, 6 days and 13 days after the formation of the burns.

The following observations were made 6 days and 13 days after the formation of the burns:

State of the burns 6 days later

The depth of the burn and the thickness of the tissue which have survived were approximately the same in the burns treated by the pomade and those which had received the control composition.

In the burns treated with the control pomade, the presence of eschars containing intact collagen fibers was noted in 6 burns. The burns treated with the pomade containing the collagenase according to the invention did not include any.

There was observed the presence of inflammatory cells infiltrated into the upper part of the dermis on 6 burns treated by the pomade with collagenase. The same observation could only be made on 3 control burns. The afflux of inflammatory cells testifies to a cicatrization process more advanced than in the burns where these infiltrations had not taken place.

There was only observed however few differences at the level of the repair of the epidermis and of the conjunctive tissue, between the treated burns and the control burns, except that this repair appeared a little more advanced in the case of the treated burns.

State of the burns 13 days later

It was observed in the treated animals that the burns were covered with a thin film of degraded tissue. New conjunctive tissue had developed over the whole of the surface of the burns, immediately under this film as well as in greater depth, in the dermis. The epidermis was developed in the form of a granulation tissue from the edges of the lesions, immediately beneath the film of degraded tissue.

It was observed in the treated lesions that the collagen portion of the eschars was dissolved by the collagenase, so that the regeneration of the conjunctive tissue could be developed at the surface, under conditions similar to those which are observed in the case of wounds through cuts. The epidermis formed can migrate over the surface of this granulation tissue.

It is observed on the contrary that the control burns are covered with deep eschars of compact collagen which adheres to the tissue and covers it. New conjunctive tissue was formed only under the new epidermis layer which formed only on the edges of the burns. The epidermis had migrated from the edges of the lesion, through the dermis, beneath the abovementioned eschars, thus separating the latter from the deep tissue. Hence, the sources of new epidermis were only observed at the edge of the lesions, which would require a surgical skin graft to ensure the complete cicatrization of these lesions.

One of the advantages of the pomade containing collagenase resides in the fact that the enzymatic treatment produces automatically a correct equilibrium between the necrotic tissues and the living tissues, which equilibrium would be difficult to recreate surgically.

The pharmaceutical preparations according to the invention can be presented in any form usable by external application: gels, emulsions, particularly such as pomades and creams, or solutions or sprayable forms (aerosols in powder), the collagenase being in each preparation associated with suitable excipients according to the particular forms. In the case of solutions for topical application, recourse is advantageously had to placing collagenase in solution in an isotonic medium, preferably a physiologically acceptable buffer of pH 7-8.5, and preferably sterile.

The collagenase preparations in the form of solutions in an injectable sterile vehicle can be administered subcutaneously, close to the wounds to be treated or to cheloids. The use of these injectable solutions can also be envisaged for deep administrations, particularly for the destruction of a pathological accumulation of collagen in the tissues, like for example in intervertebral discs.

The pharmaceutical compositions according to the invention are hence applicable to all types of lesions manifested by an uncontrolled alteration of the structures rich in collagen. By way of examples of lesions which can be treated, are burns, ulcers, eschars, hard or white eschars based on collagen, cheloids, such as those produced after surgical operations, necroses, in particular in the case of decubitus or ulcers. The pharmaceutical compositions according to the invention can also be applied preventively, particularly prior to surgical operations to form plastic or other grafts, or in operations of aesthetic surgery, and generally to any wounds of the skin.

The collagenase solutions according to the invention can also be applied to the treatment of dental caries. It is known in fact that the dental pulp is essentially formed from compact calcified collagen, dental caries being manifested by fissurization or a hole in the tooth, through which calcium escapes. The decalcified web of collagen which persists then becomes porous and risks becoming the seat of bacterial infection.

By the introduction of a concentrated solution of collagenase according to the invention into this web, the dissolution of the porous collagen is induced which can then be removed by rinsing. The action of the collagenase is interrupted by itself at the level of the healthy calcified collagen.

The collagenase solution used, buffered to pH 7-8.5, particularly with borate, contains preferably at least 1 μkat of collagenase per ml of solution. At this concentration and a fortiori for higher concentrations, the porous collagen is rapidly dissolved.

After rinsing and disinfection, the treated tooth can be closed again by applying techniques well known to the man skilled in the art. The possible residual traces of collagenase retained in the tooth are progressively inhibited by the dominating acid pH which is restored in the midst of the tooth.

As is self-evident and as results besides already from the foregoing, the invention is in no way limited to the cases which have been envisaged in the foregoing. It encompasses on the contrary all modifications, particularly those where the stabilizing properties of the collagen hydrolysates are applied with respect to any other collagenases capable of being employed in the formulation of pharmaceutical compositions. These collagenases possess at the same time, selective activities which have been defined in the foregoing and the desirable innocuousness at sufficient doses at which the selective collagenolytic activity can be manifested. In this respect the invention relates also to any association of a collagenase corresponding to the foregoing conditions, whatever the source, particularly cultures of micro-organisms from which it has been obtained, in association with collagen hydrolysates. These compositions associating the two types of principles, particularly in proportions equivalent to the preferred intervals of proportions which have been indicated, constitute equivalents of the associations more particularly claimed in some of the claims which follow.

In the same way the claims which relate more particularly to the processes of stabilization of a collagenase and more particularly of Achromase, especially by freeze-drying their solutions in the presence of collagen hydrolysates extend their effects to the stabilization of any form of collagenase, particularly on the occasion of the lyophilization of their solutions, as soon as collagen hydrolysates would be employed in the same way, particularly within the intervals of relative proportions defined above.

We claim:

1. A composition comprising:
   a collagenase which specifically recognizes a peptide sequence X-glycyl-L-prolyl in collagen in an amount effective to treat pathologies manifested by an uncontrolled alteration of collagen-rich structures in man or animal, in which X is a natural amino acid residue linked to the N-terminal end of the glycyl residue, said collagenase cutting said sequence specifically at the level of the X-glycyl linkage to degrade collagen into fragments and besides being inhibited at least partly by myosine;
   an effective amount of a neutral protease which can degrade further said collagen fragments; and
   an effective amount of an endonuclease which can contribute to the destruction of DNA released as pus by infected cells;
   the proportions of said protease and said endonuclease with respect to 0.350 μkat of said collagenase not exceeding 200 caseinolytic units for said protease and 500 nucleasic units for said endonuclease.

2. The composition of claim 1, wherein said collagenase is secreted by *Vibrio alginolyticus chemovar iophagus* in its culture medium.

3. The composition of claim 2, wherein said collagenase is secreted by the strain deposited at the C.N.C.M. under accession number I-029.

4. The composition of claim 1 which contains a dose of collagenase, expressed by the collagenase activity per weight of the composition, at least equal to 0.05 μkat/g of the pharmaceutical composition.

5. The composition of claim 1 which is a liquid solution for topical use and which contains a dose of collagenase expressed by collagenase activity per volume of liquid, at least equal to 0.05 μkat/ml.

6. The composition of claim 4 which contains from 0.1 to 2 μkat/g of collagenase.

7. The composition of claim 6 which contains from 0.5 to 1 μkat/g of collagenase.

8. The composition of claim 5 which contains from 0.1 to 2 μkat/ml of collagenase.

9. The composition of claim 8 which contains from 0.5 to 1 μkat/g of collagenase.

10. The composition of claim 1 which comprises:
    at least 0.350 μkat of said collagenase,
    20 to 200 caseinolytic units of said neutral protease and
    30 to 500 nucleasic units of said endonuclease.

11. The composition of claim 10 which comprises:
    at least 0.350 μkat of said collagenase,
    20 to 50 caseinolytic units of said neutral protease and
    30 to 60 nucleasic units of said endonuclease.

12. The composition of claim 1 which also contains a collagen hydrolysate in the proportion of from 1 to 25 parts by weight of a collagen hydrolysate per part by weight of collagenase.

13. The composition of claim 12 which contains of from 2 to 10 parts by weight of collagen hydrolysate per part by weight of collagenase.

14. The composition of claim 10 which also contains a collagen hydrolysate in the proportion of from 1 to 25 parts by weight of a collagen hydrolysate per part by weight of collagenase.

15. The composition of claim 12 which is freeze-dried and stabilized.

16. The composition of claim 1 which is in the form of a solution for use in the treatment of dental caries or other alterations of the dental pulp in man or animal.

17. A method of treating a skin burn which comprises contacting said burn with an effective amount of the composition of claim 1.

* * * * *